United States Patent [19]

Dennis

[11] 4,302,394
[45] Nov. 24, 1981

[54] PRODUCTION OF BUTYROLACTONE

[75] Inventor: Alan J. Dennis, Middlesbrough, England

[73] Assignee: Davy McKee (Oil & Chemicals) Limited, London, England

[21] Appl. No.: 139,592

[22] Filed: Apr. 11, 1980

[30] Foreign Application Priority Data

Apr. 11, 1979 [GB] United Kingdom ............... 12850/79

[51] Int. Cl.³ ............................................ C07D 307/32
[52] U.S. Cl. ................................. 260/343.6; 568/689; 568/454; 562/531
[58] Field of Search ..................................... 260/343.6

[56] References Cited

U.S. PATENT DOCUMENTS 3,868,370  2/1975  Smith ................................. 260/343.6
3,980,670  9/1976  Kummer et al. ................. 260/343.6
3,980,671  9/1976  Fernholz et al. ................. 260/343.6

OTHER PUBLICATIONS

Charles K. Brown et al., Tetrahedron Letters, No. 22, pp. 1725-1726, (1969).

Primary Examiner—Norma S. Milestone
Attorney, Agent, or Firm—Bernard, Rothwell & Brown

[57] ABSTRACT

Butyrolactone is produced by oxidizing an aldehyde-ether of the general formula:

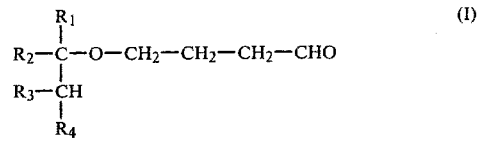

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, to form an acid ether of the general formula:

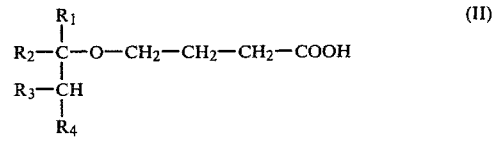

followed by deetherification, dehydration and cyclization. Oxidation can be carried out with e.g. gaseous oxygen. Deetherification can be accomplished by contact with an acid catalyst, while cyclization may occur spontaneously. A cyclic process is described in which allyl alcohol is converted by reaction with a suitable olefin, e.g. iso-butylene, to an allyl ether of a tertiary alcohol, e.g. allyl t-butyl ether, which is then hydroformylated to form the compound of formula (I), while the olefin, e.g. iso-butylene, released on deetherification of the acid ether of formula (II), is recycled to the allyl ether formation step.

10 Claims, No Drawings

PRODUCTION OF BUTYROLACTONE

This invention relates to the production of butyrolactone.

According to the present invention there is provided a process for the production of butyrolactone which comprises oxidizing an aldehyde-ether of the general formula

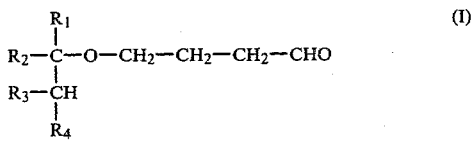

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, to form an acid-ether of the general formula:

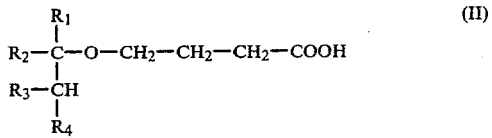

wherein $R_1$, $R_2$, $R_3$ and $R_4$ are as defined above, followed by deetherification and cyclization. Preferably $R_1$ and $R_2$ each, independently of the other, represents a methyl or ethyl group and $R_3$ and $R_4$ each, independently of the other, represents a hydrogen atom or a methyl group.

In a particularly preferred process the compound of formula (I) is:
$(CH_3)_3C-O-CH_2-CH_2-CHO$.

The reactions involved in the process of the invention are exemplified in the following reaction scheme:

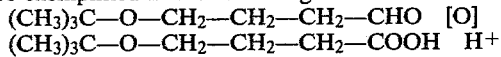

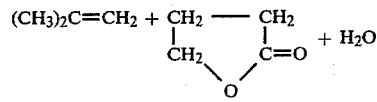

It is postulated that during the deetherification step 4-hydroxybutanoic acid is initially formed but this spontaneously cyclises to form butyrolactone and loses water in so doing.

The compounds of formula (I) can be made by hydroformylation of an allyl t-alkyl or -cycloalkyl ether of the general formula:

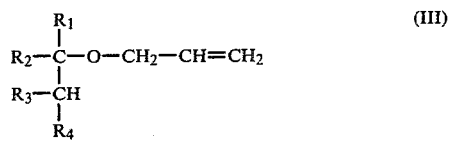

wherein $R_1$, $R_2$, $R_3$ and $R_4$ are as defined above. In this reaction the allyl ether of formula (III) is contacted with hydrogen and carbon monoxide under hydroformylation conditions in the presence of a catalytic amount of a hydroformylation catalyst. The catalyst may be any Group VIII metal-containing catalyst known to be suitable for catalysing the hydroformylation of terminal olefins. The hydroformylation conditions are selected so as to be suitable for the chosen catalyst. Further details of the production of the compounds of formula (I) can be found in copending patent application No. 139,591 by Norman Harris, Alan James Dennis and George Edwin Harrison (Case 7946), filed simultaneously herewith, the disclosure of which is herein incorporated by reference.

The allyl ethers of formula (III) can be prepared in known manner by reaction of allyl alcohol in the presence of an acidic catalyst with an olefin of the general formula:

wherein $R_1$, $R_2$, $R_3$ and $R_4$ are as defined above. As examples of olefins of the formula (IV) there can be mentioned iso-butylene, 2-methylbut-1-ene, 2-methylbut-2-ene, 2,3-dimethylbut-2-ene, 3-methylpent-2-ene, 2-ethylbut-1-ene, 1-methyl-cyclohexene and 1-methyl-cyclopentene.

Etherification of allyl alcohol can be effected by reaction with an olefin of the general formula (IV), conveniently in the presence of an acidic catalyst. The etherification is a reversible reaction and is favoured by the use of low temperatures, for example a temperature in the range of from about 0° C. to about 80° C. Usually it will be preferred to effect etherification of allyl alcohol at about 60° C. or less, preferably in the range of from about 15° C. to about 60° C. for example in the range of from about 35° C. to about 60° C. Since the olefin may be volatile it may be necessary to effect the etherification reaction under elevated pressure. Typical acidic catalysts include ion exchange resins, preferably in anhydrous form, containing sulphonic acid and/or carboxylic acid groups, such as Amberlyst 15 and Dowex 50 resins, as well as aqueous acids, e.g. aqueous solutions of phosphoric acid or dilute aqueous solutions of sulphuric acid (containing, for example, 10% w/v sulphuric acid or less), acid zeolites, acid clays, and organic acids such as p-toluenesulphonic acid or formic acid.

Deetherification of the compounds of formula (II) is conveniently accomplished by treatment with an acidic catalyst, e.g. with an aqueous acid, and acidic ion exchange resin, and acidic clay, an acidic alumina, an acidic alumino-silicate, or silica. The use of elevated temperatures is generally preferred, for example temperatures in excess of about 60° C., e.g. about 80° C. up to about 120° C. or more. Usually it will be preferred to use a temperature of not more than about 180° C. in the deetherification step. Deetherification can be carried out in the presence, but preferably in the absence, of an added inert solvent. In this step the olefin of the general formula (IV) is regenerated. Hence, according to a particularly preferred process butyrolactone is prepared by the steps comprising:

(a) reacting allyl alcohol with an olefin of the general formula (IV) in the presence of an acidic catalyst to form an allyl ether of the general formula (III);

(b) contacting resulting allyl ether of the general formula (III) with hydrogen and carbon monoxide under hydroformylation conditions in the presence of a catalytic amount of a hydroformylation catalyst;

(c) oxidizing resulting aldehyde-ether of the general formula (I) to form an acid-ether of the general formula (II);

(d) subjecting resulting acid-ether of formula (II) to deetherification, dehydration and cyclisation conditions;

(e) recovering resulting butyrolactone and regenerated olefin of the general formula (IV); and (f) recycling resulting regenerated olefin of the formula (IV) to step (a).

Recovery of butyrolactone can be effected in any convenient manner. For example, if deetherification has been effected by contact with an acidic ion exchange resin, the product butyrolactone can be recovered by distillation. On the other hand when using an aqueous acid for deetherification, the organic layer containing the product butyrolactone and possibly also unreacted tertiary material and/or solvent (if present) may be dried and distilled.

In the deetherification, dehydration and cyclisation of the compounds of formula (II) there may be formed as by-product a tertiary alcohol of the general formula:

wherein $R_1$, $R_2$, $R_3$ and $R_4$ are as defined above. Such an alcohol of the general formula (V) may be dehydrated in the presence of an acidic catalyst, such as one of those mentioned above for use in the deetherification step, to form a corresponding olefin of the general formula (IV) which can be recycled for reaction with allyl alcohol in step (a).

In the process of the invention oxidation of the aldehyde-ether of the general formula (I) can be accomplished using any suitable mild oxidising agent. Amongst oxidising agents that can be used for oxidation of aldehyde groups to carboxylic acid groups there can be mentioned alkaline permanganate solutions (e.g. alkaline $KMnO_4$ solutions). Alternatively gaseous oxygen, whether in the form of pure oxygen, oxygen-enriched air or air can be used as oxidising medium, optionally in the presence of a catalyst suitable for catalysing the oxidation of aldehydes to acids. Examples of catalyst systems suitable for catalysing oxidation of aldehydes to acids using gaseous oxygen include vanadyl sulphate, manganous acetate in acetic acid and cobalt acetate in acetic acid, as well as noble metal catalysts such as palladium on charcoal, platinum on charcoal or a hydroformylation catalyst, particularly a rhodium hydroformylation catalyst, or catalyst precursor, for example $RhH(CO)(PPh_3)_3$.

In the hydroformylation step, the hydroformylation catalyst may be any Group VIII metal-containing hydroformylation catalyst known to be effective for catalysing the hydroformylation of terminal olefins. Preferably the catalyst is a rhodium-containing catalyst comprising rhodium in complex combination with carbon monoxide and a triorganophosphine ligand, such as triphenylphosphine. When using such a catalyst the concentration of rhodium in the reaction medium may range from about 5 parts per million by weight up to about 1000 parts per million of rhodium or more, calculated as rhodium metal. Typically the rhodium concentration ranges from about 20 parts per million up to about 400 parts per million, e.g. about 40 to about 300 parts per million, calculated as rhodium metal. The reaction medium may contain excess triorganophosphine, e.g. about 2 moles up to about 1000 moles or more of excess free triorganophosphine per gram atom of rhodium. Usually the hydrogen:carbon monoxide molar ratio is approximately 1:1, e.g. about 1.05:1. The hydroformylation conditions typically include use of reaction temperatures of from about 20° C. up to about 160° C., e.g. about 70° C. to about 120° C. and use of a partial pressure of hydrogen of from about 0.1 kg/cm² absolute up to about 10 kg/cm² absolute or more and a partial pressure of carbon monoxide of about 0.1 kg/cm² absolute up to about 10 kg/cm² absolute or more. The overall pressure may be about 20 kg/cm² or less. The reaction can be effected in the presence of a solvent, e.g. a mixture of aldehyde condensation products such as is disclosed in British Patent Specification No. 1338237, or in the absence of added solvent.

The invention is further illustrated by reference to the following Examples.

EXAMPLE 1

A. Preparation of allyl t-butyl ether 50 ml allyl alcohol and 5 g dry Amberlyst 15 resin were placed in a 300 ml capacity autoclave agitated by means of a Magnedrive unit actuating an induction stirrer. (The word "Amberlyst" is a Registered Trade Mark). The autoclave was purged with iso-butylene and then warmed to 30° C. in an oil bath and pressurised to 1.75 kg/cm² absolute with iso-butylene. The pressure dropped as reaction took place and further iso-butylene was introduced to raise the pressure once again to 1.75 kg/cm². This procedure was repeated as necessary until reaction was complete after approximately 90 minutes as indicated by the cessation of uptake of iso-butylene. After releasing the pressure the product was decanted from the resin and washed several times with deionised water. The crude product was subjected to a partial vacuum to remove iso-butylene (until gas chromatography showed that there was less than 0.1% iso-butylene in the product) and then dried over anhydrous sodium carbonate. Gas chromatography, using a gas chromatograph with a flame ionisation detector and temperature programming, indicated that allyl t-butyl ether had been formed with greater than 98% efficiency. The chromatographic column was 1.83 m×3.2 mm O.D. stainless steel, packed with 10% by weight diethylene glycol succinate on Chromosorb W.

B. Hydroformylation of allyl t-butyl ether

The same autoclave was charged with the calculated quantities of $HRh(CO)(PPh_3)_3$ and $PPh_3$ and then sufficient Filmer 351 was added to bring the volume of liquid to 90 ml. (Filmer 351 is a complex mixture of polymeric condensation products of n- and iso-butyraldehydes of the type disclosed in British Patent Specification No. 1338237). The autoclave was then sealed. The body of the autoclave was immersed in an oil bath capable of being heated and thermostatically controlled to ±1° C. between 40° C. and 180° C. by means of a heater/stirrer. The pressure within the reactor could be monitored by means of a pressure transducer linked to a single pen recorder. The stirrer was switched on and its speed adjusted to 500 r.p.m. The reactor was purged with a hydrogen/carbon monoxide gas mixture, the composition of which depend on the planned $H_2$:CO ratio. The reactor was then pressurised to a level which was 0.35 kg/cm$^2$ below the desired operating pressure and isolated. The stirrer speed was then adjusted to 2000 r.p.m. and the temperature increased to the desired value. The pressure was then increased to the required level using the same $H_2$/CO mixture and the reactor isolated once more. Subsequently 10 ml. of allyl t-butyl ether were pumped into the reactor, whereupon reaction commenced. The rate of reaction was monitored by timing the pressure drop between two defined levels ±0.07 kg/cm$^2$ around the design pressure. When the pressure reached the lower defined level, the reactor was repressurised to a level 0.14 kg/cm$^2$ above the design operating pressure with an approximately 1:1 $H_2$:CO mixture as demanded by the stoichiometric requirements of the reaction and the procedure repeated until the reaction was complete, at which time the rate of pressure drop was negligible. The oil heater/stirrer was then switched off, the hot oil run out of the bath and replaced with cold oil. The oil stirrer was switched on again and the reactor cooled to 40° C. The reactor stirrer was then switched off and the reactor depressurised and opened to permit the reaction solution to be removed for analysis and/or storage.

Analysis of the reaction solution was effected utilising the gas chromatographic method outlined above in Section A. With the aid of an integrator peak areas were computed and from these results molar selectivities were calculated using response factors determined from pure compounds isolated from the reaction solution by preparative chromatography.

The results are set out in the Table.

order to cool the contents of the flask for analysis. Gas chromatographic analysis by the method outlined above in Section A indicated that the peak corresponding to 4-t-butoxybutyraldehyde had disappeared and a new peak, which was identified as 4-t-butoxybutyric acid, had appeared. The structure of this latter compound was confirmed by conversion to butyrolactone as described below. The yield of 4-t-butoxybutyric acid was calculated to be 87% of theoretical.

D. Conversion of 4-t-butoxybutyric acid to butyrolactone

To the cooled reaction solution of step C was added 1 gm of dry Amberlyst 15 resin. The oil bath temperature was raised to 100° C. and then gradually to 160° C. Gas was evolved which was identified to be iso-butylene. Analysis of the product by the gas chromatographic procedure described in Section A above indicated that the main product in the reaction mixture was butyrolactone. The yield was calculated to be 92% of theoretical based on 4-t-butoxybutyric acid. The identification of the product as butyrolactone was confirmed by comparison with an authentic sample under the chromatographic conditions employed.

EXAMPLE 2

A. Hydroformylation of allyl t-butyl ether 0.10 gms rhodium hydridocarbonyl tris(-triphenylphosphine), i.e. RhH(CO)(PPh$_3$)$_3$, 90 ml allyl t-butyl ether and 10.0 gms triphenylphosphine were charged to a 300 ml autoclave fitted with a magnetically coupled stirrer, a gas inlet dip tube and an outlet valve. The autoclave was sealed, purged with nitrogen whilst stirring its contents, and isolated. Stirring was continued whilst the temperature of the autoclave was raised to 73° C. by immersion in an oil-bath fitted with a thermostatically-controlled heater-stirrer. The autoclave was then purged with a 1:1 molar $H_2$:CO mixture and pressurised to 2.1 kg/cm$^2$ absolute by closure of the outlet

TABLE

| Run No. | Temp. °C. | Partial Pressure kg/cm$^2$ | | Rh conc. ppm | TPP conc. wt. % | Reaction Products (yield %) | | | | | | |
|---|---|---|---|---|---|---|---|---|---|---|---|---|
| | | CO | H$_2$ | | | PTBE | Unknown | trans-P(=)TBE | ATBE | cis-P(=)TBE | TBMPA | TBBA |
| 1 | 70 | 0.53 | 0.53 | 200 | 40 | 0.45 | 0.01 | 3.91 | 2.88 | 1.10 | 11.11 | 80.54 |
| 2 | 50 | 0.53 | 0.53 | 1000 | 10 | 0.73 | 0.41 | 4.87 | — | 0.84 | 17.62 | 75.53 |
| 3 | 100 | 0.53 | 0.53 | 200 | 10 | 1.27 | 0.17 | 29.72 | — | 7.43 | 8.75 | 52.66 |
| 4 | 70 | 3.79 | 3.79 | 50 | 10 | 0.86 | 0.28 | 1.05 | 1.43 | 0.35 | 28.61 | 67.42 |
| 5 | 70 | 0.53 | 0.53 | 300 | 20 | 0.74 | 0.33 | 8.57 | trace | 1.93 | 10.16 | 78.27 |
| 6 | 80 | 2.35 | 0.95 | 100 | 20 | 0.59 | 0.19 | 1.71 | 1.32 | 0.68 | 21.87 | 73.64 |

Note:
TPP = triphenylphosphine
PTBE = propyl t-butyl ether
trans-P(=)TBE = trans-propen-1-yl t-butyl ether
ATBE = allyl t-butyl ether
cis-P(=)TBE = cis-propen-1-yl t-butyl ether
TBMPA = 3-t-butoxy-2-methylpropionaldehyde
TBBA = 4-t-butoxy butyraldehyde The reaction residues from these and other experiments were combined and subjected to distillation. 4-t-butoxybutyraldehyde was obtained as a colourless liquid.

C. Oxidation of 4-t-butoxybutyraldehyde 22.2 gms 94% pure 4-t-butoxybutraldehyde and 0.1 gm HRh(CO)(PPh$_3$)$_3$ were charged to a 100 ml flask fitted with a magnetically coupled stirrer and with a reflux condenser and immersed in a thermostatically controlled oil bath. Oxygen was slowly bubbled through the solution and the oil bath temperature raised to 110° C. and held at this temperature overnight. The hot oil was then decanted and replaced with cool oil in valve. Reaction commenced and proceeded smoothly with a slight exotherm at the beginning of the reaction. As the reaction proceeded, the pressure dropped; when the total pressure reached 1.9 kg/cm$^2$ absolute, more 1:1 $H_2$:CO mixture was admitted to the autoclave to restore the pressure to 2.1 kg/cm$^2$ absolute. This repressurisation technique was repeated as necessary until no more gas was taken up, indicating that reaction was complete. This took between 3 and 4 hours. The autoclave was cooled, depressurised and opened, and the contents discharged and stored under nitrogen.

The resulting solution was analysed by gas chromatography using helium as carrier gas, a column packed with 10% w/w diethylene glycol succinate on Chromosorb PAW and a flame ionization detector. Selectivities were observed as follows:

5.6% to isomerised/hydrogenated allylic feedstock
18.9% to 3-t-butoxy-2-methyl propionaldehyde (TBMPA)
75.5% to 4-t-butoxybutyraldehyde (TBBA).

These selectivities are expressed in molar percentages.

The two aldehyde-ethers (TBMPA and TBBA) were separated by distillation from the other constituents of the reaction solution and then purified by distillation and characterised by formation of dimedone derivatives and by measurement of physical data. The following results were obtained:

| Property | TBMPA | TBBA |
| --- | --- | --- |
| Refractive index (at 23° C.) | 1.4128 | 1.4170 |
| Melting point of dimedone derivative | 107–109° C. | 133–135° C. |
| Specific gravity at 25° C. | 0.849 | 0.868 |
| Boiling point | | |
| at 743 mm Hg | 151.6° C. | 169.5° C. |
| at 760 mm Hg | 152.3° C. | 170.5° C. |
| at 100 mm Hg | 103.2° C. | 115.6° C. |

Nuclear magnetic resonance spectra were obtained for the compounds as follows, using tetramethyl silane as an internal standard and carbon tetrachloride as solvent:

| Identifying letter of C—atom to which H—atom is attached | Nature of peak | Chemical shift δ relative to TMS |
| --- | --- | --- |
| 1. TBBA (CH$_3$)$_3$C—O—CH$_2$—CH$_2$—CH$_2$—CHO | | |
|     a    b    c    d    e | | |
| a | singlet | 1.13 |
| b | triplet | 3.31 |
| c | triplet of triplets | 2.39 |
| d | doublet of triplets | 1.84 |
| e | triplet | 9.62 |
| 2. TBMPA (CH$_3$)$_3$C—O—CH$_2$—CH(CH$_3$)—CHO | | |
|     a    b   c   d   e | | |
| a | singlet | 1.16 |
| b | doublet | 3.56 |
| c | complex multiplet | 2.39 |
| d | doublet | 1.04 |
| e | doublet | 9.66. |

In each case the ratios of the peak areas corresponded to the expected ratios as predicted from the respective assigned structural formula. In the case of the doublets, triplets and multiplets the quoted chemical shift is the centred value.

B. Oxidation of 4-t-butoxybutyraldehyde 9.47 gms 95.3% pure 4-t-butoxybutyraldehyde were charged to a 50 ml round-bottomed flask and heated to 70° C. under an atmosphere of oxygen by means of an oil bath, whilst stirring by means of a magnetic stirrer and follower. Heating and stirring were continued overnight, whereupon the resulting solution was cooled and analysed by gas chromatography. 10.41 gms of product were obtained. Utilising the same gas chromatography technique as described above in Part A of this Example, this product was shown to contain 91.5% of a new compound, corresponding to a yield of 96%. The structure 4-t-butoxybutyric acid was assigned to this compound. Proof of this structure was provided by the production of butyrolactone therefrom, as described in Part C below.

C. Production of butyrolactone

The product from Part B of this Example (10.40 gms) was heated under reflux with 0.6 gms Amberlyst 15 resins at 90° C. for 3½ hrs on an oil bath whilst stirring with a magnetic stirrer and follower. The reflux condenser was supplied with coolant at −5° C. During the course of the reaction a gas was evolved which was identified as iso-butylene by gas chromatography. Analysis of the resulting solution by gas chromatography showed it to contain butyrolactone, water and t-butanol. The weight of the solution was 7.30 gms and the butyrolactone concentration in this was 63%, corresponding to a yield of 90% (4.60 gms) based upon 4-t-butoxybutyric acid. Identification of the product as butyrolactone was achieved by use of an authentic sample of butyrolactone.

EXAMPLE 3

The procedures of Parts B and C of Example 2 were repeated using air at atmospheric pressure, in place of pure oxygen as the oxidising medium in Part B, with equally good results.

EXAMPLE 4

When the procedure of Part A of Example 1 is repeated, using in place of iso-butylene, an equivalent amount of 2-methylbut-2-ene, 2,3-dimethylbut-2-ene or 1-methylcyclo-hexene, there is obtained allyl 2-methylbut-2-yl ether, allyl 2,3-dimethylbut-2-yl ether, and allyl 1-methylcyclohexyl ether respectively. Each of these compounds is used, in place of allyl t-butyl ether, in the procedure of Example 2 with similar results.

I claim:

1. A process for the production of butyrolactone which comprises oxidizing an aldehyde-ether of the general formula:

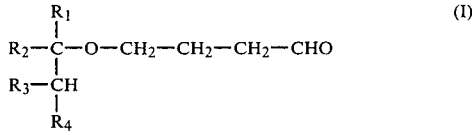

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, to form an acid-ether of the general formula:

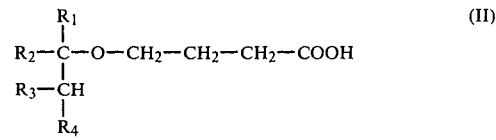

wherein $R_1$, $R_2$, $R_3$ and $R_4$ are as defined above, followed by deetherification and cyclization.

2. A process according to claim 1, in which $R_1$ and $R_2$ each represent, independently of the other, a methyl or ethyl group and $R_3$ and $R_4$ each, independently of the other, represents a hydrogen atom or a methyl group.

3. A process according to claim 1 or claim 2, in which the compound of formula (I) is:

$(CH_3)_3C-O-CH_2-CH_2-CH_2-CHO$.

4. A process according to claim 1, in which deetherification is accomplished by treatment with an acidic catalyst.

5. A process according to claim 4, in which the acidic catalyst is selected from an aqueous acid, an acidic ion exhange resin, an acidic clay, an acidic alumina, an acidic alumino-silicate and silica.

6. A proccess for the production of butyrolactone which comprises (a) reacting allyl alcohol with an olefin of the general formula:

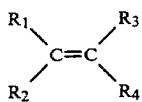
(IV)

wherein $R_1$ and $R_2$ each, independently of the other, represent a $C_1$ to $C_4$ alkyl radical, and $R_3$ and $R_4$ each, independently of the other, represent a hydrogen atom or a $C_1$ to $C_3$ alkyl radical, or wherein $R_1$ represents a $C_1$ to $C_4$ alkyl radical, $R_2$ and $R_3$ together with the carbon atoms to which they are attached form a 5-membered or 6-membered cycloaliphatic ring, and $R_4$ represents a hydrogen atom or a $C_1$ to $C_3$ alkyl radical, to form an allyl ether of the general formula:

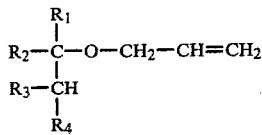
(III)

wherein $R_1$, $R_2$, $R_3$ and $R_4$ are as defined above;

(b) contacting resulting allyl ether of the general formula (III) with hydrogen and carbon monoxide under hydroformylation conditions in the presence of a catalytic amount of a hydroformulation catalyst;

(c) oxidising resulting aldehyde-ether of the general formula:

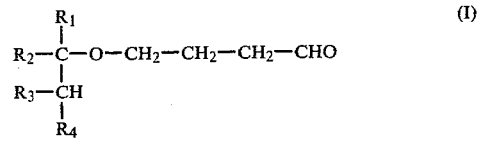
(I)

wherein $R_1$, $R_2$, $R_3$ and $R_4$ are as defined above to form an acid-ether of the general formula:

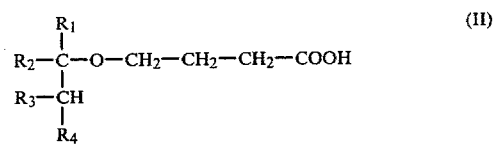
(II)

wherein $R_1$, $R_2$, $R_3$ and $R_4$ are as defined above;

(d) subjecting resulting acid-ether of the general formula (II) to deetherification, dehydration and cyclisation conditions;

(e) recovering resulting butyrolactone and regenerated olefin of the general formula (IV); and (f) recycling resulting regenerated olefin of the general formula (IV) to step (a).

7. A process according to claim 6, in which $R_1$ and $R_2$ each represents, independently of the other, a methyl or ethyl group, and $R_3$ and $R_4$ each, independently of the other, represents a hydrogen atom or a methyl group.

8. A process according to claim 6 or claim 7, in which in the compounds of the general formulae (IV), (III), (I) and (II) $R_1$ and $R_2$ are each a methyl group and $R_3$ and $R_4$ are each a hydrogen atom.

9. A process according to claim 6 or claim 7 in which the etherification of step (a) and the deetherification of step (d) are each effected in the presence of an acidic catalyst.

10. A process according to claim 6 in which oxidation is effected by use of air, oxygen-enriched air or gaseous oxygen.

* * * * *